(12) United States Patent
Arafiles

(10) Patent No.: US 6,652,526 B1
(45) Date of Patent: Nov. 25, 2003

(54) SPINAL STABILIZATION ROD FASTENER

(76) Inventor: Ruben P. Arafiles, 3228 Bansalangin St., United Paranaque Subdivision II, Paranaque City (PH), 1700

( * ) Notice: Subject to any disclaimer, the term of this patent is extended or adjusted under 35 U.S.C. 154(b) by 0 days.

(21) Appl. No.: 09/972,096

(22) Filed: Oct. 5, 2001

(51) Int. Cl.[7] .......................... A61B 17/70; A61B 17/86
(52) U.S. Cl. ........................................ 606/61; 606/73
(58) Field of Search .............................. 606/73, 61, 60, 606/54, 69, 70, 71, 72

(56) References Cited

U.S. PATENT DOCUMENTS

| | | | |
|---|---|---|---|
| 5,466,237 A | 11/1995 | Byrd, III et al. | |
| 5,562,633 A | * 10/1996 | Wozencroft | 604/171 |
| 5,562,663 A | * 10/1996 | Wisnewski et al. | 606/61 |
| 6,302,888 B1 | * 10/2001 | Mellinger et al. | 606/73 |

\* cited by examiner

*Primary Examiner*—Kevin Shaver
*Assistant Examiner*—Candice C. Melson
(74) *Attorney, Agent, or Firm*—Jack Lo

(57) ABSTRACT

A spinal stabilization rod fastener is comprised of a U-shaped bracket with a slot for receiving a spinal stabilization rod. A cavity is arranged on an interior of each arm. Inverted trapezoidal shaped lips are respectively attached to outer edges of the cavities adjacent an outer end of the slot, and directed towards an inner end of the slot. An oval bridge is arranged to be connected across the arms inside the cavities. Arcuate rims are provided on an upper surface of the bridge at the longitudinal ends. The bridge is installed by aligning it longitudinally with the slot, positioning it between the cavities, and rotating it to position its longitudinal ends in the cavities and its rims behind the lips. Rectangular slots on opposite sides of the circumference of the screw hole of the bridge allows use a flat screw driver or a suitably shaped driving tool for rotational insertion of the bridge. Modifications such as elevated portions of the arcuate rims with edges, lock against corresponding edges on the upper lips of the cavities, may allow controlled rotation of the bridge to only 90 degrees. The thickness of the bridge can be further reduced by removing a thickness equivalent to the whole thickness of the unthreaded portion of the receiving or set screw hole.

12 Claims, 4 Drawing Sheets

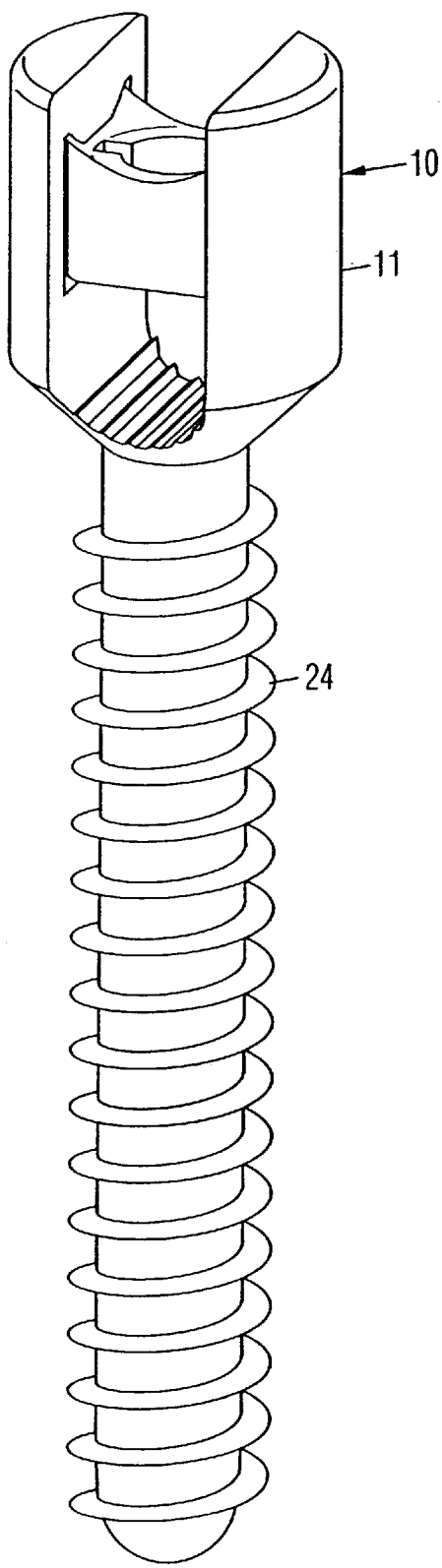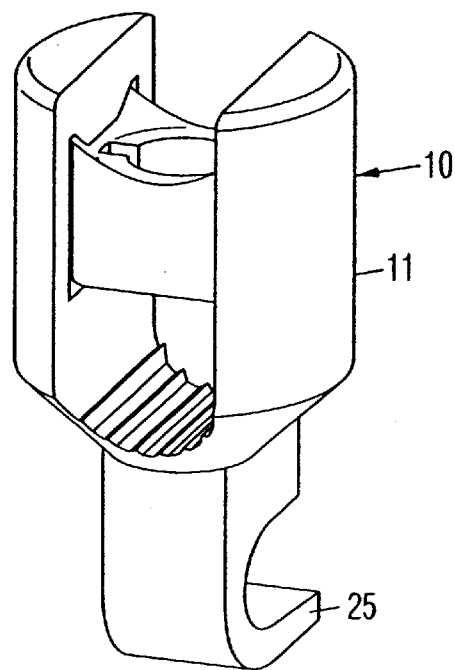
Fig. 5
Fig. 6

SPINAL STABILIZATION ROD FASTENER

BACKGROUND OF THE INVENTION

1. Field of the Invention

This invention generally relates to spinal bone implants.

2. Prior Art

Spinal bone implants are used for treating a variety of spinal conditions. A typical implant is comprised of pedicle screws inserted into the pedicles of vertebral bodies, and a rigid rod secured to the screw heads. Each pedicle screw is comprised of a U-shaped seat with a hole at the bottom and a slot between its arms, a screw extending through the hole in the seat, and a nut threaded onto an external thread around the seat. This is seen in the design of Puno et al. The implant is inserted by drilling holes in the top end of the pedicles of the vertebras. The pedicle screws are inserted such that their U-shaped seats are aligned with each other. The rod is positioned inside the slots, and the nuts are threaded onto the seats to secure the rods. A major problem with such an implant is that the nut is easily misaligned axially with the seat and cross threaded onto it. The threads on the seat and the nut may thus become damaged, and the entire implant must be replaced. Such designs may also have open or closed U-shaped channels. In closed designs, a screw hole is provided in the top portion to allow insertion of a set screw for tightening against the rod. In open designs, an oblong bridge with flanges or dovetails at the longitudinal ends is provided to allow locking of the ends of the bridge against the inner walls of the arms of the U-shaped brackets. This is typical of the Wisnewsky et al and Mellinger et al designs. A disturbing problem with these designs is the limited torque or tightening force that can be applied to the set screw because the transmitted force can spread apart or bend away the arms of the U-shaped bracket. The present invention seeks to correct this problem, without compromising ease of application, low profile, and strength of the assembly.

OBJECTIVES OF THE INVENTION

The objectives of the present spinal stabilization rod fastener are:

To develop a new mechanism for fastening a spinal stabilization rod for ease of application;

To eliminate the possibility of cross threading;

To have a low profile without sacrifing strength;

To prevent set screw forces from spreading the arms of U-shaped brackets of screw or hook assemblies;

To simplify design of instrumentation.

Further objectives of the present invention will become apparent from a consideration of the drawings and ensuing description.

BRIEF SUMMARY OF THE INVENTION

A spinal stabilization rod fastener is comprised of an oval shaped rotatable bridge arranged to be connected across the arms of U-shaped brackets, the ends of which come to lie inside cavities or slots on the inner side of the arms. The bridge has a length which is greater than the width of the slot, and a width which is narrower than the slot. Arcuate rims are provided on the upper or superior side at the longitudinal ends of the bridge. The bridge is installed by aligning it longitudinally with the U- shaped slot or rod channel, positioning it between the slots or cavities in the arms, and rotating it to position its longitudinal ends in the cavities. After rotating it to 90 degrees, the lips on the upper edge of the slots overlap the arcuate rims. The outer edges of the slots are provided with margins to prevent displacement of the installed bridge in any direction as well as to increase the strength of the arm against forces tending to spread both arms upon tightening of the set screw. Such a set screw is arranged axially through the bridge for tightening against the rod. Rectangular slots are provided on each side of the screw hole for insertion of a flat screw driver or suitably shaped driving tool. The arcuate rims can be provided with elevations on their inner surface, on one half of the rim with a sharp edge which can lock onto a corresponding edge on the upper lip of the slots to prevent rotation of the bridge to more than ninety degrees.

BRIEF DESCRIPTION OF THE SEVERAL VIEWS OF THE DRAWING

FIG. 5 is a perspective view thereof showing it with a first type of fixation device.

FIG. 6 is a perspective view thereof showing it with a second type of fixation device.

DRAWING REFERENCE NUMERALS

| | |
|---|---|
| 10. Fastener | 11. U-Shaped Bracket |
| 12. Slot | 13. Arms |
| 14. Bone Stabilization Rod | 15. Knurled Surface |
| 16. Cavities | 17. Lips |
| 18. Notches | 19. Bridge |
| 20. Arcuate Rims | 21. Driver Receiving Hole |
| 22. Set Screw | 23. Knurled Surface |
| 24. First Fixation Device | 25. Second Fixation Device |
| 26. Elevated Surface | 27. Surface Edge |
| 28. Slot Edge | 29. Rounded Depression |

DETAILED DESCRIPTION OF THE INVENTION

FIG. 1

Figures 1, 2:
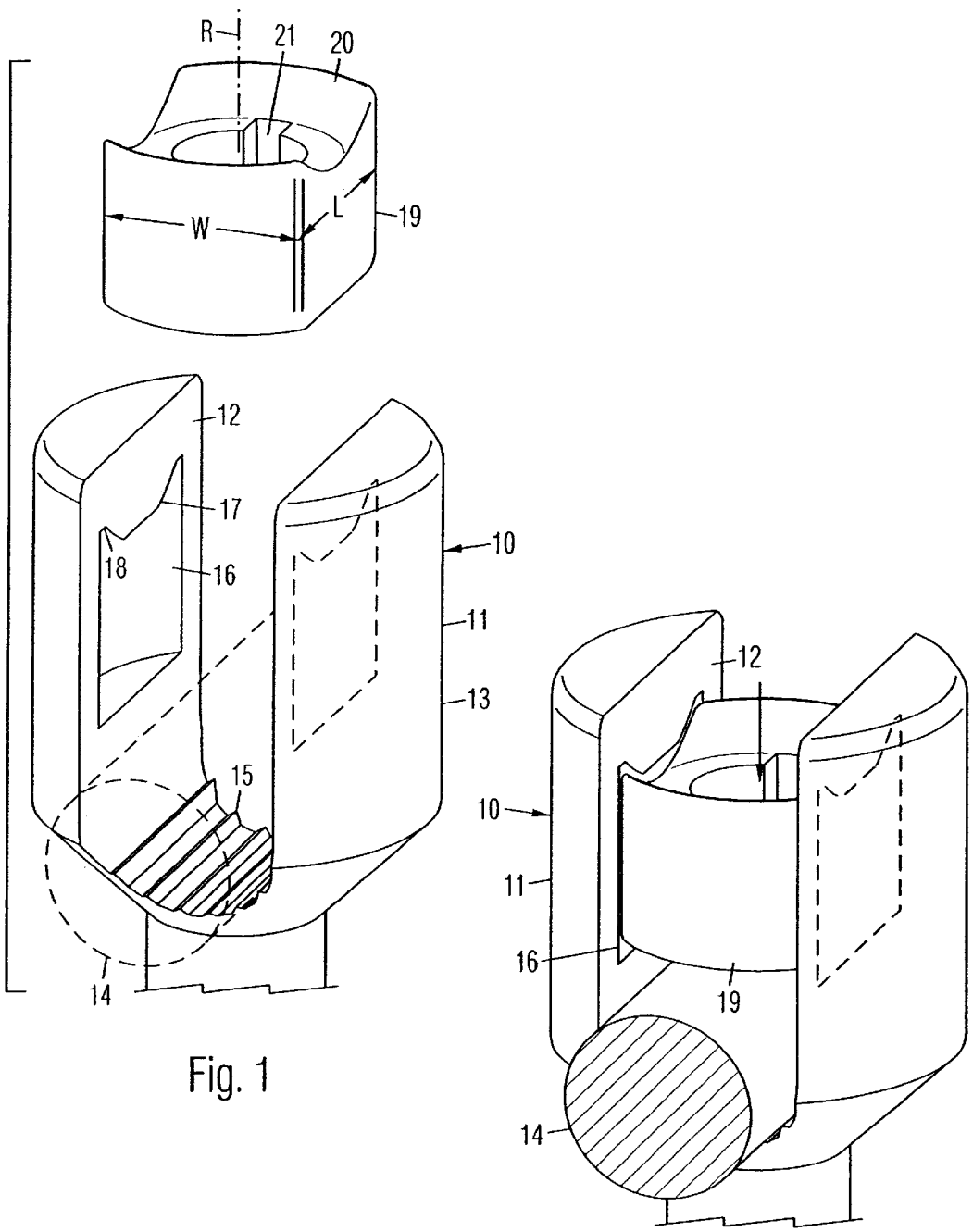
FIG. 1 is a perspective exploded view of the present bone implant fastener with a bridge separated from a U-shaped bracket thereof.
FIG. 2 is a perspective view thereof when a stabilization rod and a bridge are positioned therein.

A preferred embodiment of the present spinal stabilization rod fastener 10 is shown in a perspective exploded view in FIG. 1. It is comprised of a U-shaped bracket 11 with a slot 12 between a pair of spaced apart arms 13 for receiving a spinal stabilization rod 14. Slot 12 has an open outer end, and a closed inner end with a knurled surface 15 for grip. An opposing pair of depressions or cavities 16 are respectively arranged on interior sides of arms 13. A pair of lips 17 are respectively attached to the outer edges of cavities 16 adjacent an outer end of slot 12, and directed toward the inner end of lot 12. Notches 18 are arranged on either side of each lip 17 to define a U-shaped profile around the lip.

An oval rotatable bridge 19 is arranged to be connected across arms 13. Bridge 19 has a length L which is wider than slot 12, and a width W which is narrower than slot 12. Bridge 19 has an outer side facing open outer end of slot 12, and an inner side facing closed inner end of slot 12. Arcuate rims 20 are provided on an upper side of bridge 19 at its longitudinal ends, and are arced about a rotational axis R of bridge 19, such that the plane of rotation about the axis is parallel with the upper horizontal surface of the bridge. A driver receiving hole 21, with rectangular notches on opposite sides of the circumference, to receive a flat screw driver or suitably shaped driving tool as well as a screw with a hex head, is arranged on the upper surface of bridge 19.

Figure 3:
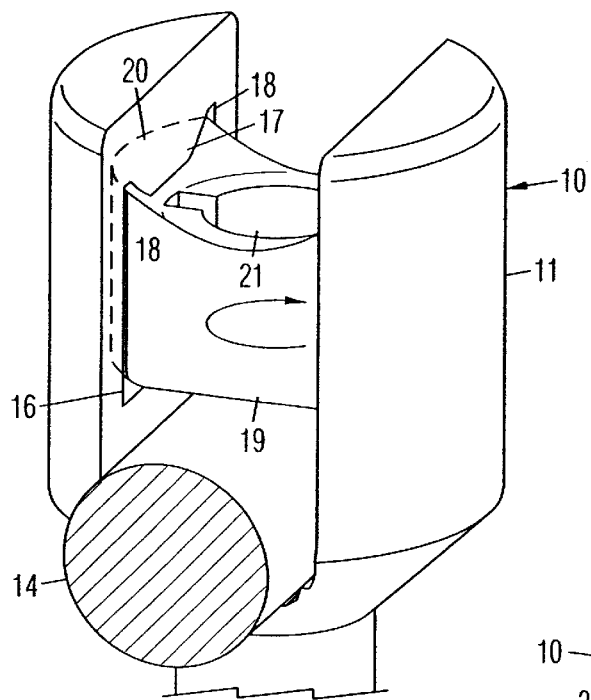
Figure 4:
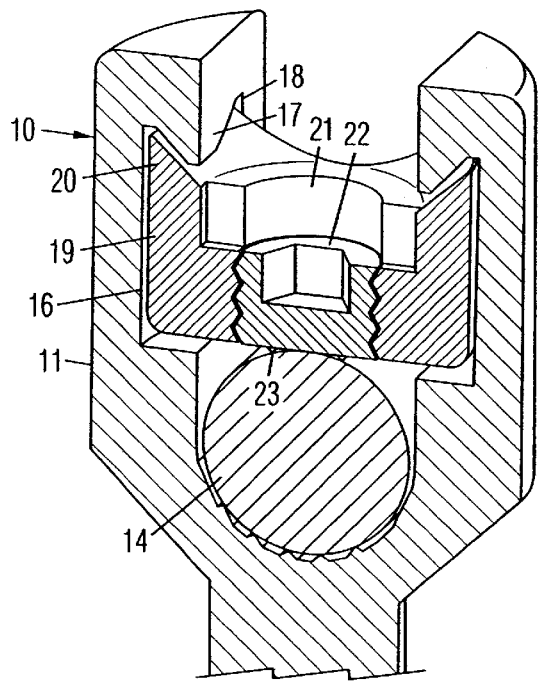
FIG. 4 is a perspective sectional view of the fastener of FIG. 3.
Figure 7:
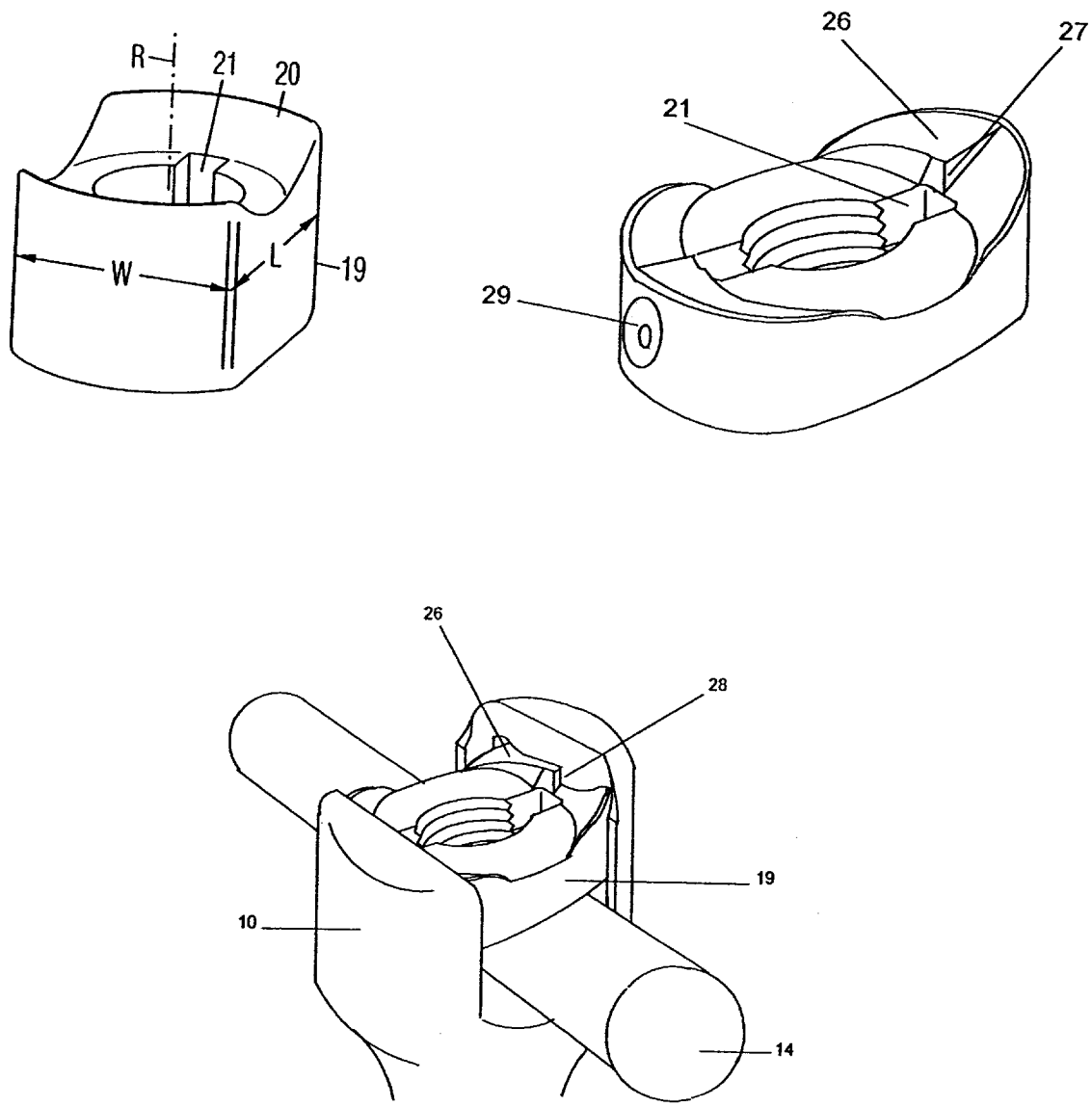
FIG. 7 is a perspective showing possible modifications on the arcuate rims of the bridge, the screw hole, and the slots on the inner wall with a view showing the installed bridge and how the upper lip of the slot prevents rotation beyond ninety degrees.

FIGS. 2–3:

As shown in FIG. 2, spinal stabilization rod 14 is positioned inside bracket 11 at the bottom of slot 12. Bridge 19 is installed by aligning it longitudinally with slot 12, and positioning it between cavities 16. As shown in FIG. 3, bridge 19 is locked inside cavities 16 by rotating it in one direction to position its longitudinal ends inside cavities 16, and arcuate rims 20 behind lips 17. Bridge 19 may be rotated by inserting a rotary driver tool, such as a flat screw driver into driver receiving hole 21.

FIG. 4:

A set screw 22 is arranged axially through bridge 19, preferably through the bottom of driver receiving hole 21. Set Screw 22 is shaped for being turned with a suitable tool, such as a hex wrench for tightening against stabilization rod 14. A knurled surface 23 is preferably provided at an inner end of set screw 22 for grip against rod 14. The inner sides of lips 17 and rims 20 where opposing surfaces meet are preferably conical for strength.

FIG.5

Fastener 10 is usually provided with different fixation devices at the inner end of U-shaped bracket 11. For example, a first fixation device 24 such as a screw in FIG. 5 may be provided for attaching directly to bone. Alternatively, a second fixation device 25 such as a hook in FIG. 6 may be provided for connecting to laminar structures of the vertebrae.

FIG. 7

Modifications can be made to bridge 19 as shown in perspective views. The modified bridge may be provided with elevations 26 in the arcuate rim to allow a square edge 27 to lock against a corresponding edge on the upper lip 28, of the slot of the bracket. This may be provided as well on the opposite rim but on the other side, so that the bridge can only be rotated to 90 degrees, on a clockwise direction. Another modification is a circular depression 29, to allow a tool with a forcep configuration and with rounded tips to hold the bridge prior to insertion. Other minor modifications include reducing the thickness of the bridge equivalent to the thickness of the previously unthreaded portion of the receiving hole 21. A perspective view with the bridge rotated 90 degrees over a stabilization rod is shown to demonstrate locking of the arcuate rim edge against the edge 28 of the upper lip of the slot.

SUMMARY AND SCOPE

Accordingly, the present spinal stabilization rod fastener is arranged to effectively secure a spinal stabilization rod. It allows easy insertion using a flat screw driver or a suitably shaped driving tool, thereby simplifying design of instrumentation, and increases the strength of the arms of the bracket against forces tending to spread them apart, compared to prior art. At the same time, low profile of the assembly is maintained. Although the foregoing description is specific, it should not be considered as a limitaton on the scope of the invention, but only as an example of the preferred embodiment. For example, elevations in the arcuate rims on opposite sides with corresponding notches on the lips may allow rotation of the bridge to only 90 degrees, for ease of insertion. The relative positions of elements can vary, and the shapes of the elements can vary. The fastener may be used to secure any other type or size of rod, and is not limited to stabilization rods. Therefore, the scope of the invention should be determined by the appended claims and their legal equivalents, not by the examples given.

I claim:

1. A rod fastener, comprising:

a U-shaped bracket for receiving a rod, wherein said U-shaped bracket is comprised of a pair of spaced apart arms with a slot there between, said slot having an open outer end, a closed inner end, and an axis extending between said inner end and said outer end;

an opposing pair of cavities arranged on respective interior sides of said arms, wherein said cavities are curved about said axis of said slot, and have respective outer edges adjacent said open outer end of said slot; and an oblong rotatable bridge positioned between said arms, wherein said bridge has a length greater than a width of said slot, a width smaller than said width of said slot, longitudinal ends which are curved about said axis of said slot, an outer side adjacent said open outer end of said slot, an inner side adjacent said closed inner end of said slot, and is arranged to be rotatable about said axis of said slot when positioned in said slot; wherein when said bridge is positioned to align said length with a longitudinal direction of said slot, said bridge is insertable into said slot, and when said bridge is positioned in said slot and rotated about said axis of said slot so that said length extends between said arms of said U-shaped bracket, said longitudinal ends of said bridge are positioned inside said cavities of said arms of said U-shaped bracket, so that said bridge is locked between said arms.

2. The rod fastener of claim 1, further including a knurled surface at said closed inner end of said slot for gripping said rod.

3. The rod fastener of claim 1, further including a screw extending from an inner end of said U-shaped bracket for attaching to an object.

4. The rod fastener of claim 1, further including a hook extending from an inner end of said U-shaped bracket for attaching to an object.

5. The rod fastener of claim 1, further including a set screw extending through said inner side of said bridge for tightening against said rod.

6. The rod fastener of claim 1, further including a driver receiving hole on said outer side of said bridge for receiving a rotary driver tool.

7. A rod fastener, comprising:

a U-shaped bracket for receiving a rod, wherein said U-shaped bracket is comprised of a pair of spaced apart arms with a slot there between, said slot having an open outer end, a closed inner end, and an axis extending between said inner end and said outer end;

an opposing pair of cavities arranged on respective interior sides of said arms, wherein said cavities are curved about said axis of said slot, and have respective outer edges adjacent said open outer end of said slot;

a pair of lips respectively attached to said outer edges of said cavities and directed toward said inner end of said slot;

a pair of notches arranged on either side of each of said lips defining a U-shaped profile around each of said lips;

an oblong rotatable bridge positioned between said arms, wherein said bridge has a length greater than a width of said slot, and a width smaller than said width of said slot, said bridge has an outer side adjacent said open outer end of said slot, an inner side adjacent said closed inner end of said slot, and is arranged to be rotatable about said axis of said slot when positioned in said slot; and arcuate rims on said outer side of said bridge at longitudinal ends of said bridge, wherein said rims are arced about said axis of said slot; wherein when said bridge is positioned to align said length with a longitudinal direction of said slot, said bridge is insertable into said slot, and when said bridge is positioned in said slot and rotated about said axis of said slot so that said length extends between said arms of said U-shaped bracket, said arcuate rims are positioned behind respective lips in said cavities, and said bridge is locked between said arms.

8. The rod fastener of claim 7, further including a knurled surface at said closed inner end of said slot for gripping said rod.

9. The rod fastener of claim 7, further including a screw extending from an inner end of said U-shaped bracket for attaching to an object.

10. The rod fastener of claim 7, further including a hook extending from an inner end of said U-shaped bracket for attaching to an object.

11. The rod fastener of claim 7, further including a set screw extending through said inner side of said bridge for tightening against said rod.

12. The rod fastener of claim 7, further including a driver receiving hole on said outer side of said bridge for receiving a rotary driver tool.

* * * * *